(12) United States Patent
Myasoedov et al.

(10) Patent No.: US 7,576,202 B2
(45) Date of Patent: Aug. 18, 2009

(54) TRITIUM-TRACED SAXITOXIN DIHYDROCHLORIDE AND METHOD FOR THE PRODUCTION THEREOF

(75) Inventors: Nikolay Fedorovich Myasoedov, Moscow (RU); Valery Pavlovich Shevchenko, Moscow (RU); Igor Yulianovich Nagaev, Moskovskaya obl. (RU); Alexander Susan, Leawood, KS (US)

(73) Assignee: Institut Molekulyarnoi Genetiki Rossiiskoi Akademh Nauk (IMG RAN) (RU)

( * ) Notice: Subject to any disclaimer, the term of this patent is extended or adjusted under 35 U.S.C. 154(b) by 62 days.

(21) Appl. No.: 11/722,926

(22) PCT Filed: Dec. 27, 2005

(86) PCT No.: PCT/RU2005/000672

§ 371 (c)(1),
(2), (4) Date: Nov. 1, 2007

(87) PCT Pub. No.: WO2006/071138

PCT Pub. Date: Jul. 6, 2006

(65) Prior Publication Data

US 2008/0091013 A1 Apr. 17, 2008

(30) Foreign Application Priority Data

Dec. 27, 2004 (RU) ................ 2004138131

(51) Int. Cl.
*C07D 491/00* (2006.01)
(52) U.S. Cl. .................................. 544/251
(58) Field of Classification Search .......... 544/251
See application file for complete search history.

(56) References Cited

U.S. PATENT DOCUMENTS

| 3,892,847 A | 7/1975 | Adams et al. |
| 4,001,413 A | 1/1977 | Adams et al. |

FOREIGN PATENT DOCUMENTS

| RU | 1649779 | | 4/1993 |
| RU | 1121928 | * | 3/1994 |
| RU | 2233285 | | 7/2004 |

OTHER PUBLICATIONS

"Synthesis of new highly radioactive tetrodotoxin derivatives and their binding properties to the sodium channel"; Robert Chicheportiche et al.; Eur. J. Biochem, 1980, 104, 617-625.
"Binding of [$^3$H]batrachotoxinin A-20-α-benzoate and [$^3$H]saxitoxin to receptor sites associated with sodium channels in trout brain synaptoneurosomes"; Jared R. Rubin et al.; Comparative Biochemistry and physiology, Part C: Pharmacology, toxicology & Endocrinology, 1993, 105C(2), 231-8.
International Preliminary Examination Report, with annexes and English translation of amended pages and conclusion of the IPER (13 pages).
International Search Report; PCT/RU2005/000672; Apr. 20, 2006.

* cited by examiner

*Primary Examiner*—James O Wilson
*Assistant Examiner*—Erich A Leeser
(74) *Attorney, Agent, or Firm*—Fish & Richardson P.C.

(57) ABSTRACT

The invention relates to a tritium-traced saxitoxin dihydrichloride of formula (I) whose radioactivity ranges from 15-31 Ci/mmol and to a novel method for introducing tritium into a molecule comprising stages required for introducing tritium label by isotope exchange associated with the obtainment of a stably-traced radioactive preparation which can be used, in particular for receptor binding analyses.

17 Claims, 2 Drawing Sheets

TRITIUM-TRACED SAXITOXIN DIHYDROCHLORIDE AND METHOD FOR THE PRODUCTION THEREOF

FIELD OF THE INVENTION

The invention relates to the field of organic chemistry and may find use in analytic chemistry, bioorganic chemistry, biochemistry and applied medicine.

STATE OF THE ART

Saxitoxin (*The Merck Index*, 11 ed., Budavari. S.; O'Niel, M. J.; Smith, A.; Heckelmann, P. E., Eds., Merck & Co.; Rahway, 1989, compound No. 8344, p. 1330), the cyclic system of which is typical for the whole family of guanidine biotoxins, was first isolated in a sufficiently pure form from mollusk *Saxidomus giganteus* (E. J. Schantz, J. D. Mold, D. W. Stanger, J. Shavel, F. J. Riel, J. P. Bowden, J. M. Lynch, R. Savage Wyler, B. Riegel, H. Sommer "Paralytic Shellfish Poison. VI. A Procedure for the Isolation and Purification of the Poison from Toxic Clam and Mussel Tissues," published in the J. Am. Chem. Soc. Vol. 79 N. 19 (1957), pp. 5230-5235). Presumptions concerning the structure of saxitoxin were made in the document by W. Schuett, H. Rapoport "Saxitoxin, the Paralytic Shellfish Poison. Degradation to a Pyrrolopyrimidine" in J. Am. Chem. Soc. Vol. 84, N. 11 (1962) pp. 2266-2267. The later-established structure of this compound was presented in the article of E. J. Schantz, V. E. Ghazarossian, H. K. Schnoes, F. M. Strong, J. P. Springer, J. O. Pezzanite, J. Clardy "Structure of saxitoxin" in the J. Am. Chem. Soc. Vol. 97, N. 5 (1975 pp. 1238-1239.

In sea water saxitoxin in dangerous concentrations is isolated by different dinoflagellates (Dinophyta)—microscopic algae, the accumulation of which is provided for by the so-called "red tides." Further absorption and accumulation of toxin in the organisms of mollusca, Crustacea and fish create a serious threat of mortal danger of being poisoned among consumers of this product not only in the U.S.A., but also in Japan and Europe. In fresh water saxitoxin may be formed and isolated by some blue-green algae and possibly cyanobacteria, which may also threaten the well-being of people in areas where such water is consumed.

At the present time 12 main toxins of the saxitoxin group have been identified, the structure and generally accepted abbreviated designations of which are presented below

|   | R1 | R2 | R3 | R4 |   |
|---|---|---|---|---|---|
| 1 | H | H | H | H | STX |
| 2 | H | H | H | $SO_3^-$ | B1 |
| 3 | H | $OSO_3^-$ | H | H | GTX2 |
| 4 | H | $OSO_3^-$ | H | $SO_3^-$ | C1 |

|   | R1 | R2 | R3 | R4 |   |
|---|---|---|---|---|---|
| 5 | H | H | $OSO_3^-$ | H | GTX3 |
| 6 | H | H | $OSO_3^-$ | $SO_3^-$ | C2 |
| 7 | OH | H | H | H | NEO |
| 8 | OH | H | H | $SO_3^-$ | B2 |
| 9 | OH | $OSO_3^-$ | H | H | GTX1 |
| 10 | OH | $OSO_3^-$ | H | $SO_3^-$ | C3 |
| 11 | OH | H | $OSO_3^-$ | H | GTX4 |
| 12 | OH | H | $OSO_3^-$ | $SO_3^-$ | C4 |

Saxitoxin and analogs thereof are strong toxins inhibiting a number of vitally important processes in the organism of mammalians. First of all it became known that saxitoxin inhibits the transport of sodium, mainly through potential-dependent sodium channels, which was shown in earlier studies (G. S. Wiberg, N. R. Stephenson, Toxicol. Appl. Pharmacol., vol. 2 (1960), p. 607) and used later (see, for example, G. Strichartz, J. Gen. Physiol., vol. 84, 1984, pp. 281-305). Since sodium channels play an important role in the appearance and development of serious neuro-degenerative and cardiovascular diseases, a study of their functioning is a way to understand the pathogenesis of those diseases and to develop new efficient medicaments.

One of the methods of studying is to make an analysis of the binding of radioactive ligand to corresponding receptors. This method, as compared with the well-recommended biological method of study (on mice), has the advantages of higher sensitivity (by 2-3 orders) and productivity. Since the end of the 1970s, the method has become very widely used for the study of the properties of sodium channels present in different organs and tissues of mammals (see, for example the article by E. Moczydlowski, V. M. Olivera, W. R. Gray, G. R. Strichartz "Discrimination of muscle and neuronal Na-channel subtypes by binding competition between [$^3$H]saxitoxin and mu-conotoxins," published in the Proc. Natl. Acad. Sci. USA Vol. 83 N. 14, 1986, P. 5321-5325). However, a significant obstacle to a more wide-spread distribution is the absence of a water-soluble form of saxitoxin or an analog thereof with a level of radioactivity that is sufficient and stable in an aqueous medium (the report "The Receptor Binding Assay for the Saxitoxins: Importance, Impediments and Solutions," presented by S. Hall at a conference of a Workshop on the Use of Receptor binding Assay (RBA), 1-5 Sep. 2003).

A water-soluble saxitoxin dihydrochloride of formula (I) is known from the state of the art (I)

$$\begin{bmatrix} H_2N \diagdown \diagup O \\ O \diagup \diagdown \diagup \\ HN \diagdown \diagup H \diagup N \\ H_2\overset{+}{N} \diagdown N \diagup NH \diagup \diagdown OH \\ OH \end{bmatrix} 2\ HCl$$

One of the first methods of introducing a tritium label into a saxitoxin molecule by isotope exchange with tritium water was proposed by J. M. Ritchie, R. B. Rogart and G. R. Strichartz ("A new method for labeling saxitoxin and its binding to non-myelinated fibres of the rabbit vagus, lobster walking leg, and garfish olfactory nerves." J. Physiol. Vol. 261, Issue 2, 1976, pp. 477-494). This method makes it possible to obtain saxitoxin traced exclusively to position 11. However, this label is not stable as a result of an exchange of a hydrogen atom in this position with water both in the storage period and in the conditions of the experiment. A product with a level of radioactivity of 39 Ci/mmol, produced by the Amersham firm and comprising a tritium traced saxitoxin, is not stable during storage either. Therefore, there is a need for a stable water-soluble saxitoxin traced derivative, which up to the present time has not been satisfied. A tritium-traced saxitoxin with a degree of radiochemical purity of more than 95% is required for use in receptor binding analysis.

BACKGROUND OF THE INVENTION

Different methods for introducing tritium into organic compounds are known, among which isotope exchange, hydration (including selective) and hydrodehalogenation are preferable. Wherein, the exchange reaction with the participation of gaseous tritium is most preferable for the preparation of tritium-traced saturated and aromatic compounds. A review of the methods for introducing tritium is presented, in particular, in the publication by V. P. Shevhcenko, I. Yu. Nagaev, N. F. Myasoedov "Liphophilic compounds labeled with tritium (Chapter 3)." Moscow, Nauka, 2003.

A solid-phase isotope exchange is the most preferable method of introducing a tritium label into saxitoxin, since it does not require the synthesis of special precursors. However, in order to introduce tritium into this compound, conditions should be selected under which saxitoxin is not destroyed. Furthermore, it is known from prior art that in tritium hydrogenation reactions on palladium heterogeneous catalysts, the curves "yield of a radioactive product vs temperature" with a fixed residence time and "yield of a radioactive product vs residence time" upon a fixed temperature pass through maximum (H. W. Cook, W. E. M. Lands, Can. J. Biochem., vol. 53, 1975, p. 1220). Therefore, an important object is also optimization of the conditions of the process for achievement of a product yield that is close to maximum. Taking the aforesaid circumstances into account and carrying out a systematic study, the authors of the instant invention have developed a method for introducing tritium into a saxitoxin molecule in order to prepare a stably-traced product and synthesized tritium-traced saxitoxin satisfying the aforesaid requirements.

SUMMARY OF THE INVENTION

The instant invention relates to tritium-traced saxitoxin dihydrochloride of formula (I)

(I)

$$\begin{bmatrix} H_2N \diagdown \diagup O \\ O \diagup \diagdown \diagup \\ HN \diagdown \diagup H \diagup N \\ H_2\overset{+}{N} \diagdown N \diagup NH \diagup \diagdown OH \\ OH \end{bmatrix} 2\ HCl$$

having a radioactivity of 15-31 Ci/mmol.

The invention also provides a new method for introducing tritium into a saxitoxin molecule by isotope exchange, the method comprising the following steps:

a) loading a solid phase obtained by combining a source of saxitoxin with a catalyst comprising a metal of group 10 of the Periodic Table of Elements in a ratio of the catalyst:source of saxitoxin from 100 to 200 into a reactor, vacuumizing the reactor to a residual pressure of from 0.05 Pa to 0.5 Pa and introducing into the reactor a source of gaseous tritium to achievement of the initial pressure in the range of 200-500 GPa;

b) heating the reaction mixture from step (d) in the reactor to a temperature of from 100 to 180° C. and carrying out a reaction at the indicated temperature during a period of time from 5 minutes to 30 minutes;

c) isolating a product comprising [$^3$H]saxitoxin from the reaction mixture and purifying the isolated product.

DETAILED DESCRIPTION OF THE INVENTION

The instant invention relates to stably tritium-traced saxitoxin or to a water-soluble salt thereof, such as dihydrochloride. The authors of the invention prepared a tritium-traced saxitoxin preparation with a molar radioactivity of 15-31 Ci mmol and radiochemical purity of more that 97%. The obtained traced saxitoxin passed testing within the frame of the NOAA Marine Biotoxins program in the U.S.A. and Chile. The studies showed that the traced preparation satisfies the requirements stipulated in respect to radioactive reagents for receptor binding analyses, in particular it has a very low unspecific binding. As a result it was recommended by the National Ocean Service, Charleston (U.S.A.), the Center of Food Products Safety of the US FDA and by the International Atomic Energy Agency (IAEA) for the analysis of saxitoxin in sea products. The created preparation may also find use as a traced analytic reagent for a study of the properties of subtypes of sodium channels which are present in the tissues of different organs of humans and other animals in place of the existing traced reagents which are distinguished by instability. The radioactivity of the product is 15-20 Ci/mol, preferably the radioactivity of the product is 25-31 Ci/mol. The radiochemical purity of the product exceeds 95%, preferably the radiochemical purity of the product exceeds 97%.

In accordance with the method of preparing the tritium-traced saxitoxin, presented by the instant invention, saxitoxin should be introduced into an isotope exchange reaction in the form of a free base or in the form of a salt thereof with acid. In order to carry out the reaction, a source of gaseous tritium and a heterogenic catalyst, comprising a transition metal of group 10 of the Periodic System of elements is used in an edition recommended by the IUPAC in 1989. Since saxitoxin molecules have not only easily protonated nitrogen and oxygen atoms, but also two positively charged fragments, the reaction of saxitoxin molecules with tritium in these conditions will take place mainly near the keto group of the compound, which increases the stability of the obtained toxin.

Any product enriched to a sufficient degree with saxitoxin or a salt thereof may be used as a source of saxitoxin. A salt formed from inorganic acid, such as hydrochloric acid, hydrobromic acid, sulfuric acid, chloric acid and other acceptable acids, is preferable as the salt. However, a salt formed from an organic acid may be used with the proviso that the hydrogen atoms of the organic acid are subjected to solid-phase catalytic isotope exchange with tritium in a significantly less degree than saxitoxin. Such an organic acid may be benzenesulfonic acid, p-toluene sulfonic acid, trifluoroacetic acid and other acceptable acids. Most preferable are inorganic acids, in particular, hydrogen haloid acids.

It is most preferable to use a product enriched with saxitoxin and comprising a free base of saxitoxin or dihydrochloride thereof. The content of the saxitoxin in the source of saxitoxin as calculated to a free base is 85% (by weight) or more, preferably 90% (by weight) and most preferably 95% (by weight) or more.

Any suitable gas enriched to a sufficient degree with tritium may be a source of gaseous tritium for conduction of the reaction in accordance with the instant invention, with the proviso that the ballast components of this gas do not have an undesirable effect on the activity of the catalyst, in particular, are not known catalytic poisons for catalysts on the base of transition metals. Preferably, molecular hydrogen enriched with tritium is a source of tritium. A more preferable source of tritium is molecular hydrogen highly enriched with tritium. Most preferable is molecular tritium with a high degree of purity.

A palladium catalyst is a preferable heterogenic catalyst for an isotope exchange reaction, the catalyst comprising a transition metal of group 10 of the Periodic system of elements. A more preferable palladium catalyst is a catalyst comprising metal palladium applied onto the substrate of a material that is stable in respect to external actions, such as activated carbon and carbon fibres, calcium carbonate, barium sulfate, kieselguhr, zeolites and other substrates known to a person skilled in the art. An even more preferable such catalyst is Pd/BaSO$_4$, comprising 3-15% (by weight) of palladium. It is most preferable in the indicated reaction to use a restored Pd/BaSO4 catalyst with a palladium content of about 5% (by weight).

An isotope exchange reaction may be carried out with different meanings of the temperature and initial pressure of tritium in the reaction system. The temperature in the course of the reaction should preferably be retained within the range of 100-180° C., more preferably within the range of 100-160° C. The reaction may be carried out at a reduced initial pressure of the gaseous tritium or at a pressure close to atmospheric. In particular, in view of the cost of the product and the safety of carrying out the reaction, a reduced initial pressure of the gaseous tritium is preferable. A more preferable initial pressure is about 333 GPa.

It is preferable to carry out the isotope exchange reaction in a two-phase "gas-solid substance" system, wherein it is more preferable that the source of saxitoxin would be a solid phase together with a catalyst. It is most preferable when the source of saxitoxin is combined with the catalyst by the method of impregnating the catalyst and evaporating the solvent.

In order to impregnate, the source of saxitoxin should be dissolved in the solvent, for which a mainly alcohol solvent should be used. A lower aliphatic alcohol or a mixture of such alcohols, for example ethanol, methanol and mixtures thereof is a preferable alcohol solvent. The most preferable is methanol. Evaporation of the solvent is preferably carried out at a reduced pressure, for example by a rotary evaporator. The solid residue obtained as a result, which comprises a catalyst combined with a source of saxitoxin is preferably subjected to lyophilization before it is introduced into the isotope exchange reaction.

The reaction is preferably carried out in a sealed reactor at a predetermined initial pressure of the tritium and catalyst: source of saxitoxin ratio. In laboratory scales, the reactor is preferably an ampoule to be filled, in which a source of saxitoxin, combined with a catalyst, and a source of gaseous tritium are placed. It is most preferable to first load into the ampoule the catalyst combined with the source of saxitoxin and to carry out the step of vacuumizing the ampoule prior to filling the ampoule with gaseous tritium and sealing it. The residual pressure in the ampoule after the vacuumization may be from 0.05 Pa to 0.5 Pa. The residual pressure is preferably from 0.05 Pa to 0.2 Pa. Most preferably the residual pressure is about 0.1 Pa. The ranges of the initial values of the pressure of tritium were given consideration above.

As regards the catalyst:source of saxitoxin ratio, the isotope exchange reaction may be carried out at a catalyst:source of saxitoxin ratio of from 100 to 200. A ratio of from 100 to 150 is preferable, while about 100 is the most preferable.

The length of the reaction depends on many factors, among which, in the first place, the initial pressure of tritium, the temperature in the reaction system and the activity of the catalyst should be indicated. A person skilled in the art, having given consideration to the specification of the instant invention, by conducting routine experiments within the scope of his qualifications is capable of determining the time of termination of the reaction. As a guide for action, the authors of the instant invention note that from 5 minutes to 30 minutes is usually required for the course of the reaction with achievement of the acceptable degree of conversion. A preferable time is from 5 to 20 minutes, the most preferable time is from 5 to 15 minutes.

The use of chromatography, preferably liquid chromatography, is preferable in order to isolate the product containing [$^3$H]saxitoxin from the reaction mixture. More preferable is the use of high-performance liquid chromatography with reversed phase (RP-HPLC) with isocratic elution by the first eluent. The makeup of the eluent, in the first place, depends on the type and properties of the stationary phase and may be determined and optimized by a person skilled in the art, after giving consideration to the specification of the instant invention, by routine experimentation within the scope of his qualification. As a guide, the authors of the instant invention note that an eluent may be prepared on the base of standard buffer solutions with the addition of insignificant amounts of aliphatic alcohols and other generally accepted components for example, on the basis of a 50 mM standard buffer (pH 2.8) with the addition of 1% isopropanol. Prior to chromatographic isolation with RP-HPLC, it is preferable to carry out preliminary filtration of the reaction mixture by means of a short column comprising modified silica gel.

In order to purify a reaction mass in order to obtain a product having a sufficient degree of radiochemical purity, it is preferable to use highly effective liquid chromatography with reversed phase (RP-HPLC) with isocratic elution by a second eluent. The makeup of the second eluent preferably differs from the makeup of the first eluent. It may be determined and optimized by a person skilled in the art, after giving consideration to the specification of the instant invention, by routine experimentation within the scope of his qualification. As a guide, the authors of the instant invention note that an eluent may be prepared on the base of standard buffer solutions with the addition of insignificant amounts of aliphatic alcohols and other generally accepted components for example, on the basis of a 15 mM $NH_4OAc$ buffer (pH 5) with the addition of 1% isopropanol.

In the case where saxitoxin in the form of a base is added into the isotope exchange reaction, then in order to obtain a water-soluble form of saxitoxin, a reaction of the obtained product with a suitable inorganic acid, preferably with a hydrohalide acid and most preferably with a hydrochloric acid. For this, a solution of the necessary acid in a suitable solvent comprising a corresponding amount of the acid may be used. For example, the ratio of monobasic acid:purified saxitoxin trace may be 2 moles of acid per a mole of the saxitoxin base. In the case of an acid with greater basicity of the acid, recalculation is obvious to a person skilled in the art. The preparation of the desired salt may be carried out by mixing the product of the isotope exchange reaction, comprising a certain determined by analysis amount of the desired compound, with a corresponding amount of acid taken in the form of a solution in a suitable solvent. Suitable solvents are, for example, water, lower aliphatic alcohols and any mixtures thereof.

Alternatively, if the acid is volatile, an excess of a solution of such an acid with subsequent moderate heating of a reaction mixture, preferably at a reduced pressure, may be used in order to remove the excess of the volatile acid, which has not entered the reaction. Volatile hydrochloric acid is preferable. Alternatively, if a salt with organic acid is required, for example, to enhance the delivery of cells to a live organism or culture, such a salt of organic acid may be formed, for example, with asparagine acid, arginine acid, ascorbic acid and other acceptable acids with the use of methods well-known to a person skilled in the art.

In the most preferable variants of the invention, preliminarily restored, dispersed 5% $Pd/BaSO_4$ with ratios of the catalyst-toxin from 100 to 200, at temperatures from 100 to 160° C., were used to prepare traced saxitoxin, the reaction being carried out for from 5 to 15 minutes.

Figure 1:
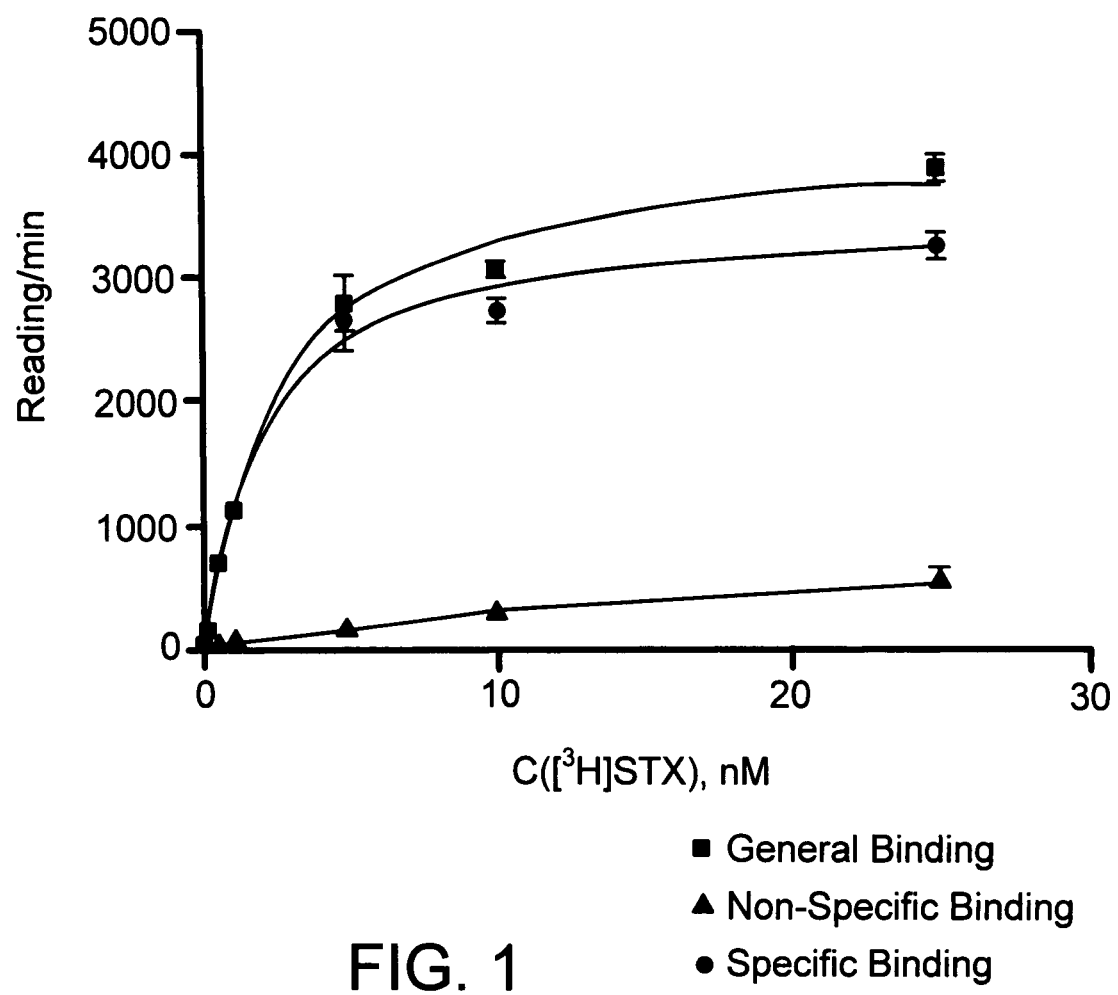
FIG. 1 shows a curve of saturation for determination of the binding parameter $K_D$.

Further, the invention will be explained with reference to examples presented exclusively for the purposes of illustration. Therefore, these examples of realization of the invention should not be given consideration as limitations of the scope of the invention determined by the set of claims of the invention, which is set forth further below.

EXAMPLE 1

Preparation of Purified Tritium-traced Saxitoxin Preparation

A solution of 0.5 mg of saxitoxin dihydrochloride in 0.05 ml of methanol was added to 50 mg of 5% (by weight) $Pd/BaSO_4$. Methanol was removed by evaporation on a rotary evaporator and the solid residue was lyophilized. A catalyst with a substance applied thereon was transferred into a reaction ampoule. Then the ampoule was vacuumized until a residual pressure of 0.1 Pa was reached, filled with gaseous tritium until a pressure of 333 GPa was reached and held at a temperature of 100° C. for 15 min. The excess gaseous tritium was then removed by vacuumization. The substance was extracted from the catalyst by methanol (5×2 ml) and separated by filtering through a layer of LiChroSorb C18, 30-40 μm. Labile tritium was removed, several times dissolving the substance in methanol (5×2 ml) and evaporating the latter.

Preparative purification of the traced preparation was carried out by the HPLC method on a Zorbax SB-AQ C18, 4.6×150 mm column with the use of 1% isopropanol in 50 mM standard buffer (pH 2.8)+2 mM PSNa: after 9 min—washing with 1 ml of methanol. The retention time of the saxitoxin—3.19 min. Repeated HPLC was carried out in a system of 15 mM $NH_4OAc$ (pH 5)+1% isopropanol+2 mM of hexansulfonate.

The yield of the traced preparation: 60-70%, molar radioactivity: 15-20 Ci/mmol, radiochemical purity: 98-99%.

EXAMPLE 2

Preparation of Tritium-traced Saxitoxin at High Temperature

A solution of 0.5 mg of saxitoxin dihydrochloride in 0.05 ml of methanol was added to 100 mg of 5% $Pd/BaSO_4$. The methanol was removed by evaporation on a rotary evaporator and the solid residue was lyophilized. The catalyst with the substance applied on it was transferred to a reaction ampoule. Then the ampoule was vacuumized until a residual pressure of 0.1 Pa was reached, filled with gaseous tritium until a pressure of 333 GPa was reached and held at a temperature of 160° C. for 5 min. The excess of gaseous tritium was removed by vacuumiztion. The substance was extracted from the catalyst by methanol (5×2 ml) and separated by filtering through a layer of LiChroSorb C18, 30-40 μm. The labile tritium was removed, dissolving the substance several times in methanol (5×2 ml) and the latter was evaporated. The yield of the traced preparation: 6-9%, the molar radioactivity; 25-31 Ci/mmol, the radiochemical purity: 98-99%.

EXAMPLE 3

Receptor Binding Analysis with use of the Obtained [$^3$H]Saxitoxin

A preparation was used in the analysis that comprises [$^3$H]saxitoxin ($^3$H STX), which has a specific activity of 20 Ci/mmol at a concentration of 0.1 mCi/ml and a radiochemical degree of purity of more than 97% according to the standard analysis HPLC, which are determined within the frame of the NOAA Marine Biotoxins program.

In accordance with the protocol of analysis with the receptor PSP, the meaning of $K_D$ equal to 2.0 nM was determined from the saturation of binding curve, which agrees with literature data and the results obtained for the preceding [$^3$H] saxitoxin samples. The unspecific binding was extremely low (FIG. 1).

Figure 2:
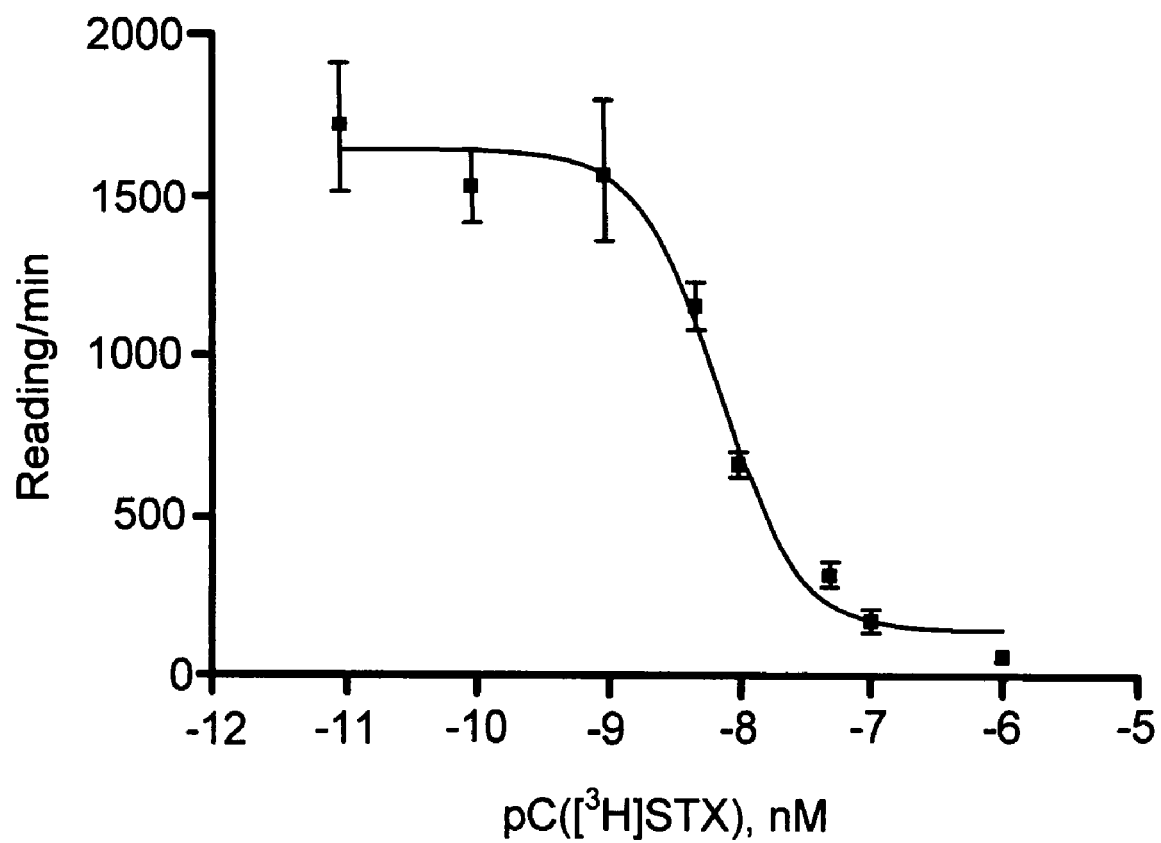
FIG. 2 shows a sigmoidal "dose-response" curve for determination of binding parameters—the Hill coefficient and $IC_{50}$.

In an experiment on microplates, carried out in accordance with a study protocol approved by the IAEA/NOAA/FDA Technology Transfer Project, a concurrent binding curve was obtained, carrying out the calculation with the aid of a Wallac Microbeta scintillation counter (FIG. 2). The Hill coefficient equal to −0.9 and also the value of $IC_{50}$ equal to 5.4 nM were determined from the obtained data by the regressive analysis methods. For the quality control QC sample (nominal meaning of $IC_{50}$ is 3.0 nM), studied under the same conditions, the meaning $IC_{50}$ equal to 3.11 nM was determine from a similar curve.

The results of studies convincingly show that the preparation obtained in accordance with the instant invention satisfies the requirements stipulated in respect o such reagents (Hill coefficient [0.8-1.2]; QC 3.0±20%).

The invention claimed is:

1. A tritium-traced saxitoxin dihydrochloride of formula (I)

$$\left[\begin{array}{c} \text{H}_2\text{N}\diagdown\text{O}\diagdown\text{...structure...} \end{array}\right] \cdot 2\,\text{HCl} \quad (I)$$

having a radioactivity of 15-31 Ci/mmol.

2. The tritium-traced saxitoxin dihydrochloride according to claim 1, wherein the radioactivity is 15-20 Ci/mmol.

3. The tritium-traced saxitoxin dihydrochloride according to claim 1, wherein the radioactivity is 25-31 Ci/mmol.

4. A method for introducing tritium into a saxitoxin molecule, the method comprising the following steps:
  (a) loading a solid phase obtained by combining a source of saxitoxin with a catalyst comprising a metal of group 10 of the Periodic Table of Elements in a ratio of the catalyst:source of saxitoxin from 100 to 200 into a reactor, vacuumizing the reactor to a residual pressure of from 0.05 Pa to 0.5 Pa and introducing into the reactor a source of gaseous tritium to achievement of the initial pressure in the range of 200-500 GPa;
  (b) heating the reaction mixture from step (d) in the reactor to a temperature of from 100 to 180° C. and carrying out a reaction at the indicated temperature during a period of time from 5 minutes to 30 minutes;
  (c) isolating a product comprising [$^3$H]saxitoxin from the reaction mixture and purifying the isolated product.

5. The method according to claim 4, wherein the source of saxitoxin is a substance comprising not less than 90% (by weight) of saxitoxin.

6. The method according to claim 5, wherein the source of saxitoxin is a substance comprising not less than 95% (by weight) of saxitoxin.

7. The method according to claim 4, wherein in step (a) the metal catalyst comprises palladium applied onto a substrate of a material stable against external action.

8. The method according to claim 7, wherein in step (a) the metal catalyst comprises 5-15% (by weight) of palladium applied onto a substrate of a material stable against external action, such as activated carbon and carbon fibres, calcium carbonate, barium sulfate, kieselguhr or zeolites.

9. The method according to claim 8, wherein in step (a) the metal catalyst comprises about 5% (by weight) of palladium applied onto a substrate of barium sulfate and is a reduced catalyst.

10. The method according to claim 4, wherein the solid phase is obtained by impregnating the catalyst with an alcohol solution comprising a source of saxitoxin with subsequent evaporation of the solvent.

11. The method according to claim 10, wherein the alcohol solvent is ethanol, methanol and mixtures thereof, preferably methanol.

12. The method according to claim 4, wherein the reactor is a sealable ampoule, vacuumization is carried out to a residual pressure of about 0.1 Pa, while the initial pressure of the source of gaseous tritium is equal to about 333 GPa.

13. The method according to claim 4, wherein in step (b) the reaction mixture is heated to a temperature of from 100 to 160° C. and the reaction is carried out at the indicated temperature for a period of time from 5 minutes to 20 minutes.

14. The method according to claim 13, wherein in step (b) the reaction mixture is heated to a temperature of about 100° C. and the reaction is carried out at the indicated temperature for a period of time of about 15 minutes.

15. The method according to claim 13, wherein in step (b) the reaction mixture is heated to a temperature of about 160° C. and the reaction is carried out at the indicated temperature for a period of time of about 5 minutes.

16. The method according to claim 4, wherein in step (c) in order to isolate a product comprising [$^3$H]saxitoxin from the reaction mixture RP-HPLC is used with isocratic eluetion by the first element.

17. The method according to claim 16, wherein in step (c) purification of the product is carried out by the RP-HPLC method with isocratic eluetion by the second eluent, wherein the makeup of the second eluent differs from the makeup of the first eluent.

* * * * *